United States Patent [19]

Johnson

[11] 4,396,015
[45] Aug. 2, 1983

[54] MEDICATION CONTROL DEVICE FOR USE IN TREATING LUNGS

[76] Inventor: Robert J. Johnson, 3430 Glasgow Cir., Riverside, Calif. 92503

[21] Appl. No.: 218,953

[22] Filed: Dec. 22, 1980

[51] Int. Cl.³ .............................................. A61M 16/00

[52] U.S. Cl. ........................... 128/200.14; 128/204.26

[58] Field of Search ....................... 128/200.14, 200.18, 128/200.21, 204.25, 204.26, 204.23

[56] References Cited

U.S. PATENT DOCUMENTS

| | | | |
|---|---|---|---|
| 2,535,844 | 12/1950 | Emerson | 128/200.21 |
| 3,537,448 | 11/1970 | Liston | 128/200.21 |
| 3,580,249 | 5/1971 | Takaoka | 128/200.14 |
| 4,030,492 | 6/1977 | Simbruner | 128/200.21 |
| 4,253,468 | 3/1981 | Lehmbeck | 128/200.18 |
| 4,261,355 | 4/1981 | Glazener | 128/204.25 |
| 4,265,237 | 5/1981 | Schwanbom et al. | 128/204.25 |
| 4,279,250 | 7/1981 | Valenta et al. | 128/200.14 |

*Primary Examiner*—Henry J. Recla

[57] ABSTRACT

An airway device having a first passage open at one end to the atmosphere and carrying a mouthpiece at the other end through which a patient may breathe. A second passage opens into the first passage for communication with the outlet of a medication nebulizer. The airway device also has a tubular section extending into the first passage for communication with the negative air pressure sensing port of a positive pressure breathing machine which upon sensing inhalation by the patient causes actuation of the nebulizer to apply the nebulized medication through the airway device to the patient's lungs during the inhalation phase only of each breathing cycle while allowing the patient to breathe freely into the atmosphere.

4 Claims, 8 Drawing Figures

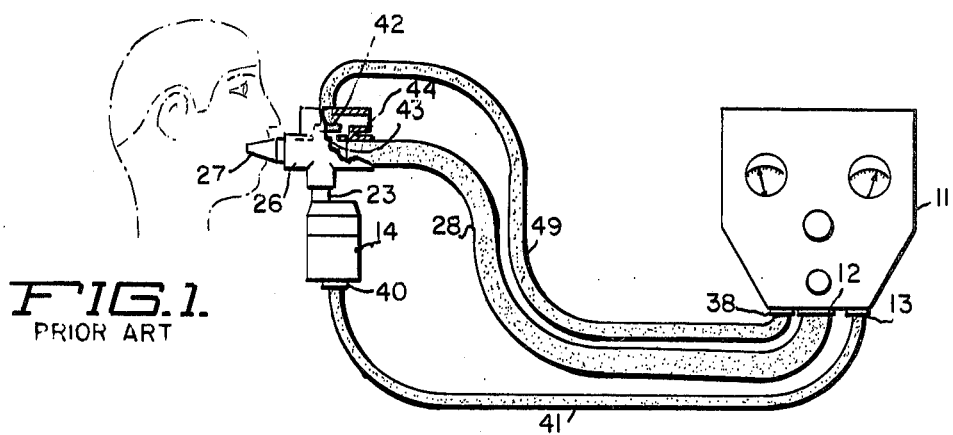
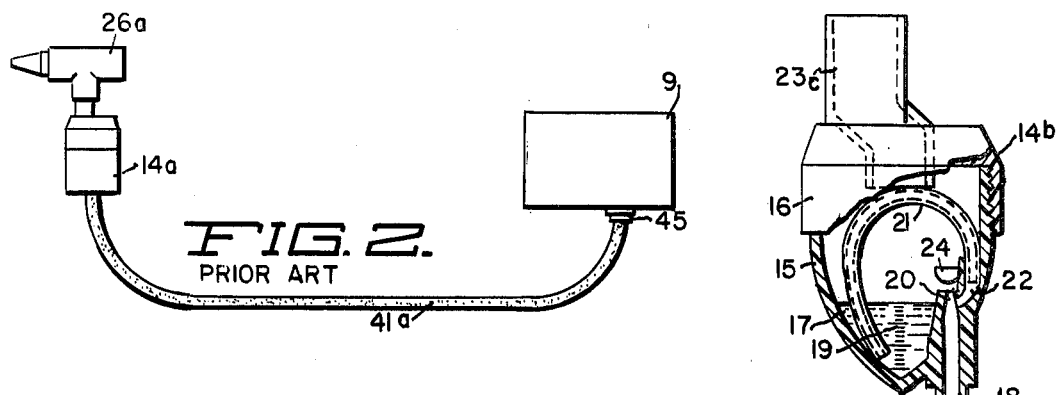
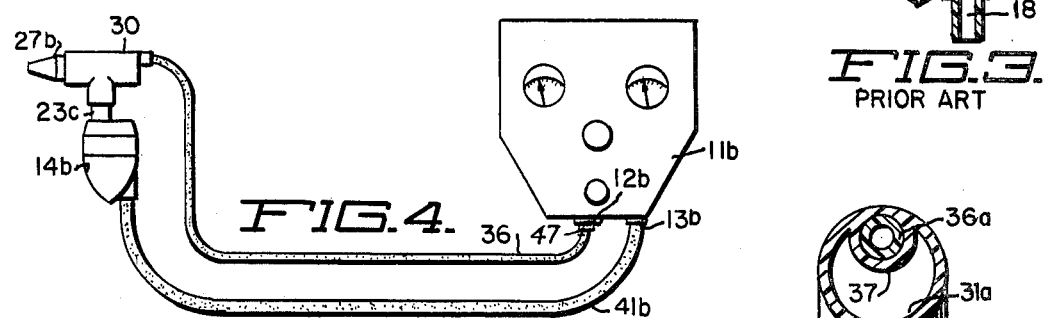
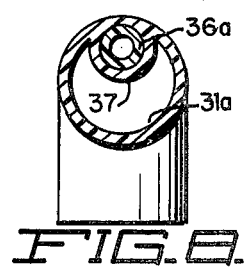
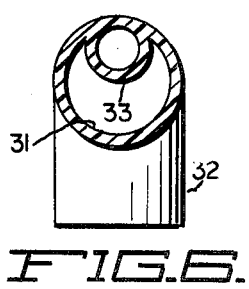
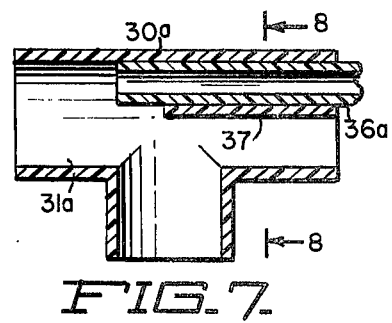

MEDICATION CONTROL DEVICE FOR USE IN TREATING LUNGS

BACKGROUND OF THE INVENTION

1. Field of the Invention

This invention relates to the treatment of diseases of the respiratory system and associated parts of the anatomy, such as the heart, and has particular reference to apparatus for controlling the administration of aerosolized medication into the lungs of a patient.

2. Description of the Prior Art

Respirator machines, such as the well-known intermittent positive pressure breathing machine (IPPB), are extensively used in the treatment of patients having lung or allied diseases, such as asthma, emphysema, heart trouble, etc. Such machines have an air outlet which may be connected through a suitable breathing tube to a mouth-piece held in the patient's mouth. Included in the machine is a highly sensitive control device which senses inhalation by the patient, and the resulting negative air pressure, as referenced from the ambient atmospheric pressure, causes the machine to apply a positive pressure flow of air through a T-connection or the like to the mouthpiece to assist the patient during such inhalation phase of each breathing cycle. The machine is also normally responsive to the control device upon sensing negative pressure to apply positive air pressure to the inlet port of a medication nebulizer. The outlet of the nebulizer is connected to an inlet branch of the T-connection. When air passes through the T-connection to the patient's lungs, it causes an aspiration effect which, combined with positive pressure applied to the nebulizer inlet, causes the nebulizer to nebulize a quantity of liquid medication which is admitted to the mouthpiece and is thus introduced into the patient's lungs. During exhalation, the resulting positive pressure developed in the breathing tube causes the control device to disable the nebulizer.

Although the above system is generally satisfactory, it is highly desirable that those patients who are strong enough to carry on their natural breathing functions be allowed to do so while still receiving nebulized medication from the nebulizer. In such cases, the breathing tube is usually removed so that the patient can breath directly to and from the atmosphere through the mouthpiece and T-connection, and the IPPB machine is replaced by a suitable source of pressurized air or oxygen. Therefore, the medication will be nebulized and inhaled during the inhalation phase of the breathing cycle. However, since the machine will continuously apply a positive pressure to the inlet of the nebulizer, much of the medication is wasted since during the exhalation phase of the breathing cycle it is blown out into the atmosphere. Such waste is aggravated by the fact that the period of exhalation is normally of longer duration than the period of inhalation.

Of prime importance in this regard is the fact that it is generally highly desirable to measure the amount of medication entering the patient's lungs or to apply a specific measured amount of such medication. However, with the aforementioned system, the amount cannot be accurately measured since an unknown amount is wasted and therefore the actual amount entering the patient's lungs can only be estimated.

It therefore becomes the principal object of the present invention to provide means for applying medication to a patient's lungs during the inhalation phase only of a breathing cycle while allowing free breathing of the patient to and from the atmosphere without applying positive pressure to the lungs.

Another object is to provide a means for accurately measuring the amount of medication applied to a patient's lungs while permitting free breathing of the patient to and from the atmosphere.

Another object is to utilize an intermittent positive pressure breathing machine and a nebulizer controlled thereby to apply medication to a patient's lungs during inhalation only while permitting free breathing of the patient to and from the atmosphere.

SUMMARY OF THE INVENTION

According to the present invention, a T-connection or similar air way device is provided having a first passage therethrough which is open at one end to the atmosphere and is intended to be breathed into by the patient at the opposite end. A second passage opens into the first and is intended to be connected to the outlet of a nebulizer, preferably of the passive type, wherein a quantity of liquid medication or the like is nebulized when positive air pressure is applied to an inlet port of the nebulizer. Such nebulizers, per se, are well-known in the art.

The T-connection or air way device of the present invention also includes a tubular sensing section which extends into the first passage but is of smaller cross sectional area and opens into the first passage at a point preferably intermediate the ends the first passage whereby, during the inhalation phase of the breathing cycle, a negative air pressure will be applied to the tubular section. Such tubular section is connected at its opposite end to the pressure sensing device of the above noted intermittent positive pressure breathing machine. In such machine, application of a negative pressure to its pressure sensing device causes positive liter flow to be applied to the inlet port of the nebulizer. Thus, during the inhalation phase of a breathing cycle, negative air pressure will be applied through the air way device to cause the breathing machine to apply a liter flow to the inlet port of the nebulizer while not restricting the free breathing action of the patient. The nebulizer will accordingly nebulize a portion of the liquid medication therein and will enable such nebulized medication to be drawn into the patient's lungs.

During the exhalation phase of the breathing cycle, positive air pressure is applied to the tubular sensing section of the air way device, also without interferring with the patient's free breathing action. This is sensed by the sensing device of the machine to cut off positive air pressure to the nebulizer and thus arrest nebulization whereby to prevent loss of medication into the atmosphere. This cut-off of medication will also occur during periods of rest, i.e., during the periods between the inhalation and exhalation phases.

BRIEF DESCRIPTION OF THE DRAWING

The manner in which the above and other objects of the invention are accomplished will be readily understood on reference to the following specification when read in conjunction with the accompanying drawing, wherein:

FIG. 1 is a schematic view illustrating a prior known medication administering system in which breathing air is transferred to and from a patient through an intermittent positive pressure breathing apparatus, and nebulized medication is administered only during the inhalation phase.

FIG. 2 is a schematic view illustrating another previously known medication administering system in which the patient is permitted to breath freely into the atmosphere without positive pressure being applied to the lungs but in which a continuous positive air pressure created by a compressor or other suitable source of pressurized air or oxygen is applied to the inlet of the nebulizer.

FIG. 3 is a sectional view through a conventional nebulizer which may be used in connection with the present invention.

FIG. 4 is a schematic view illustrating a nebulized medication administering system according to the present invention.

FIG. 5 is a longitudinal sectional view through an air way device embodying a preferred form of the present invention.

FIG. 6 is a transverse sectional view taken along line 6—6 of FIG. 5.

FIG. 7 is a sectional view similar to that of FIG. 5 but illustrating a modified form of the invention.

FIG. 8 is a transverse sectional view taken along the line 8—8 of FIG. 7.

DESCRIPTION OF THE PRIOR ART

FIG. 1 illustrates a prior system which has been used extensively for administering medication to a patient's lungs. Such system employs a conventional intermittent positive pressure breathing (IPPB) machine generally indicated at 11. One such machine is commercially available from the Puritan Bennett Corporation of Kansas City, Missouri, under the trade name Puritan Bennett PR-1.

Machine 11 has a control port 12 and a liter flow outlet port 13. Application of negative air pressure (below ambient atmospheric pressure) to the control port 12 will result in positively pressurized air being applied to both ports 12 and 13. Concurrently, positive air pressure will be applied to a third port 38. Cut-off of negative air pressure or application of positive air pressure to control port 12 will result in the port 12 being closed and air pressure being cut off from ports 13 and 38.

The respirator apparatus also includes a conventional nebulizer generally indicated at 14 having an inlet port 40 connected by a flexible tube 41 to the outer port 13 of the machine 11.

An outlet port 23 of the nebulizer is connected to one passage of a T-connector or air way device 26 which has another passage communicating with the first and connected at one end to a mouthpiece 27 through which the person may breath. The opposite end of the latter passage is connected by a flexible large-bore tube 28 to the control port 12 of the machine 11.

An exhalation valve 42 in the form of an expandible bellows whose interior is connected by tube 49 to port 38 is arranged to seat against a valve port 43 in the connector 26 to seal off the interior of the connector from the atmosphere during an inhalation phase. When the patient exhales, positive air pressure is removed from the interior of valve 42 by the machine 11, enabling the valve to open and permitting the patient to exhale through the valve port 43 and through an opening 44 into the atmosphere.

When the patient inhales, negative pressure is applied through the connector 26 and tube 28 to cause the machine to apply positive air flow through the tube 28, thus reinforcing the patient's inspiratory process, and concurrently to apply positive pressure to the nebulizer 14, causing administration of nebulized medication into the patient's lungs. When a preset pressure is reached the cycle is completed and the machine turns off.

Although the above system works satisfactorily in some cases, positive air pressure applied to the lungs can have a deleterious effect on the cardiovasculor system and, when possible, should be replaced by a system which can apply nebulized or aerosolized medication without having to apply air pressure to the lungs.

FIG. 2 illustrates another prior art system which has been used heretofore to apply nebulized medication while permitting the patient to breath freely into the atmosphere. Here, an air compressor or other suitable source of pressurized air or oxygen 9, nebulizer 14a which is similar to nebulizer 14, tube 41a, and a T-connector or air way device 26a may be used.

A pressure outlet port 45 of the source 9 is connected by a flexible small diameter tube 41a to the inlet port of the nebulizer 14a. However, the tube 28 of FIG. 1 is removed, permitting the person to breath freely into the atmosphere. In this case, the source 9 must be arranged to continuously apply positive air pressure through the tube 41a to the nebulizer 14a. Thus, during both the inhalation and the exhalation phases, nebulized medication is introduced into the T-connector 26a. Accordingly, during the exhalation phase of a breathing cycle, the nebulized medication is expelled into the atmosphere and wasted. Thus, and particularly since the exhalation phase differs in length of time from the inhalation phase, it is not possible to measure the amount of medication actually introduced into the patient's lungs.

DESCRIPTION OF THE PREFERRED EMBODIMENT OF THE INVENTION

According to the present invention, the same type IPPB machine 11b as in FIG. 1 is used. A somewhat similar and conventional nebulizer 14b (FIGS. 3 and 4) is employed. The latter comprises a transparent cup 15 enclosed by a cap 16 and containing a supply of liquid medication 17. A scale 19 on the side of the cup 15 provides a means for measuring the quantity of medication within the cup. An inlet port 18 forms a nozzle 20 for emitting a jet of air upwardly into the cup. A curved siphon tube 21 is mounted in the cup 15 and has one end immersed in the liquid 17 and the other end connected to a passage 22 opening into the nozzle 20. Upon application of positive air pressure to the inlet port 18 through machine outlet port 13b and tube 41b, a jet of air is injected into the cup which is effective to aspirate a small quantity of the liquid medication 17 and to impinge the same against a partly spherical head 24 which is effective to finely nebulize the liquid. The resulting mist is drawn off through the outlet port 23c. However, an improved air way device 30 (FIGS. 4,5, and 6) is provided. The latter is preferably molded of transparent rigid plastic and has a first cylindrical passage 31 extending therethrough and communicating with a second cylindrical passage 32 extending at right angles thereto and being of substantially the same diameter. The left hand end of passage 31 is adapted to frictionally receive a suitable mouthpiece 27b and the passage 32 is adapted to frictionally receive the outlet port 23c of the nebulizer 14b.

A tubular section 33 is molded integrally with the air way 30 and extends within the passage 31 and preferably opens into the latter passage 31 intermediate the left hand end of passage 31 and the second passage 32. Such tubular section 33 extends along the length of the passage 31 and terminates in a reduced diameter section 35 which extends past the right hand end of the passage 31 to receive one end of a flexible small-diameter tube 36 which is connected at its opposite end to the port **12*b* of the machine 11*b* through a suitable adapter 47. Although the diameter of the passage of tubular section 33 may be varied as desired, it has been found that good results are obtained when such diameter is on the order of one third the diameter of the passage 31**.

During inhalation by the patient, the negative air pressure resulting within the passage 31 will be transmitted through the passage 31 to draw in air from the atmosphere. Also, such reduced air pressure will be transmitted through the tubular section 33 and tube 36 to control port **12*b* of the machine 11*b*, causing the latter to apply positive air pressure through tube 41*b* to the nebulizer 14*b*. This causes the nebulizer to concurrently introduce the nebulized medication into the air way 30 from whence it is drawn into the patient's lungs. During exhalation, positive air pressure is introduced in the air way device 30 and this is sensed through the tubular section 33 and tube 36, causing the machine to cut off positive pressure to the nebulizer 14*b***, thus stopping the flow of nebulized medication so that none will be wasted into the atmosphere.

DESCRIPTION OF THE ALTERNATIVE EMBODIMENT OF THE INVENTION

FIGS. 7 and 8 illustrate a modified form of the invention in which a tubular guide way 37 is formed in the passage **31*a* of the air way 30*a* to guide the left hand end of tube 36*a* connected to the control port of the breathing machine. Tube 36*a* frictionally engages the inner surface of the guide way 37 and may be adjusted lengthwise to vary the distance between the left hand end thereof and the left hand end of passage 31*a*** to provide appropriate air coupling for sensing negative air pressure of different magnitudes as may be required for different breathing machines or for use in connection with different patients, such as children, having different degrees of inhalation and exhalation air flows.

I claim:

1. For use in combination with an apparatus of the type which applies nebulized medication to an outlet port upon sensing a negative air pressure in a pressure sensing port thereof, the improvement which comprises, an air way device having a first passage through which a patient may inhale and exhale, said device having a second passage for communicating said first passage with said outlet port, and tubular means for connecting said sensing port with a portion only of said first passage, the remainder of said first passage being open to the atmosphere and said tubular means being in air coupled relation to said first passage whereby said patient may inhale and exhale freely to and from the atmosphere and said apparatus will apply said nebulized medication to said air way device during inhalation only of said patient, said air way device having an integral annular guideway extending within said first passage, and said tubular means being slidably mounted in said guideway for endwise adjustment.

2. An apparatus for delivering medicated air to a patient wherein the apparatus is connectible to a machine which supplies pressurized air in response to a pressure signal at a control port, said apparatus comprising:

an air way device having a first passage, said first passage having first port means which is open to the atmosphere and second port means adapted to communicate with the patient's respiratory system whereby the patient may inhale atmospheric air through said first passage and exhale to the atmosphere through said first passage;

said air way device having nebulizer port means communicating with said first passage;

a nebulizer outside said first passage for supplying medication to the first passage, said nebulizer being adapted to be coupled to the machine; means for coupling the nebulizer to the nebulizer port means whereby the nebulizer can supply medication through the nebulizer port means to the first passage;

said air way device having sensing port means opening into said first passage;

said port means being the only openings to the first passage through which fluid can be supplied to the first passage whereby the pressure conditions in the first passage are controlled by the patient's respiration and the sensing port senses said pressure conditions;

means for coupling the sensing port to the control port of the machine whereby the machine can provide pressurized air to the nebulizer to operate the nebulizer in accordance with pressure sensed by the sensing port; and said means for coupling the nebulizer to the nebulizer port means including a second passage in the air way device intersecting said first passage intermediate the ends thereof, said air way device including tubular means in said first passage extending along the length thereof and terminating in said sensing port between said nebulizer port means and said second port means, and means coupled to the air way device for providing a mouthpiece at the second port means.

3. An apparatus as defined in claim 2 wherein the cross-sectional area of said second passage is substantially the same as the cross-sectional area of the first passage and said tubular means has a cross-sectional area smaller than the cross-sectional area of the first passage.

4. An apparatus as defined in claim 2 wherein said tubular means is molded integrally with said air way device.

* * * * *